(12) United States Patent
Zarinetchi et al.

(10) Patent No.: US 6,324,430 B1
(45) Date of Patent: *Nov. 27, 2001

(54) MAGNETIC SHIELD FOR PRIMARY COIL OF TRANSCUTANEOUS ENERGY TRANSFER DEVICE

(75) Inventors: Farhad Zarinetchi, Chelmsford; Stephen J. Keville, Harvard; Robert M. Hart, Arlington, all of MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/110,608

(22) Filed: Jul. 6, 1998

(51) Int. Cl.[7] ................................................. H02J 17/00

(52) U.S. Cl. ............................................................ 607/61

(58) Field of Search ................................ 607/61, 60, 30, 607/32; 600/9, 13, 14, 15

(56) References Cited

U.S. PATENT DOCUMENTS

| | | |
|---|---|---|
| 3,195,540 | 7/1965 | Waller ................................. 128/422 |
| 3,357,434 | 12/1967 | Abell . |
| 3,824,129 | 7/1974 | Fagan, Jr. ................................. 136/6 |
| 3,888,260 | 6/1975 | Fischell ................................. 128/419 |
| 3,934,177 | 1/1976 | Horbach ................................. 317/100 |
| 3,942,535 | 3/1976 | Schulman ............................. 128/419 |
| 4,012,769 | 3/1977 | Edwards et al. ....................... 357/81 |

(List continued on next page.)

FOREIGN PATENT DOCUMENTS

| | | | |
|---|---|---|---|
| 2720011 | 11/1978 | (DE) | ................................. A61N/1/36 |
| 0507360 | 7/1992 | (EP) | ................................. H01F/23/00 |
| 7046164 | 2/1995 | (JP) | ................................. H04B/5/00 |

OTHER PUBLICATIONS

Matsuki et al. "Energy Transferring System Reducing Temperature Rise for Implantable Power Consuming Devices".

Geselowitz et al. "The Effects of Metals on a Transcutanous Energy Transmission System" Sep. 1992.

Miller et al. "Development of an Autotuned Transcutaneous Energy Transfer System" 1993.

Mitanmura et al. "Development of Transcutaneous Energy Transmission System".

Mussivand et al. "Transcutaneous Energy Transfer System Performance Evaluation" May 1993.

Mussivand et al. "Remote Energy Transmission for Powering Artificial Hearts and Assist Devices".

Sherman et al. "Energy Transmission Across Intact Skin for Powering Artificial Internal Organs" 1981.

Abe, "Development of Transcutaneous Energy Transmission System for Totally Implantable Artificial Heart," (1988).

(List continued on next page.)

*Primary Examiner*—Kennedy Schaetzle
(74) *Attorney, Agent, or Firm*—Nutter, McClennen & Fish LLP

(57) ABSTRACT

A transcutaneous energy transfer device is provided which has a magnetic shield covering the primary winding of the device to reduce sensitivity of the device to conducting objects in the vicinity of the coils and to increase the percentage of magnetic field generated by the primary coil which reaches the secondary coil. This shield is preferably larger than the primary coil in all dimensions and is either formed of a high permeability flexible material, for example a low loss magnetic material in a flexible polymer matrix, with perforations formed in the material sufficient to permit ventilation of the patient's skin situated under the shield, or the shield may be formed of segments of very high permeability material connected by a flexible, porous mesh material.

52 Claims, 2 Drawing Sheets

U.S. PATENT DOCUMENTS

| | | | | |
|---|---|---|---|---|
| 4,041,955 | | 8/1977 | Kelly et al. | 128/419 |
| 4,068,292 | * | 1/1978 | Berry et al. | 361/437 |
| 4,071,032 | * | 1/1978 | Schulman | 607/36 |
| 4,104,701 | | 8/1978 | Baranowski | 361/386 |
| 4,441,498 | | 4/1984 | Nording | 128/419 |
| 4,517,585 | | 5/1985 | Ridout et al. | 357/81 |
| 4,539,433 | | 9/1985 | Ishino et al. | 174/35 MS |
| 4,586,508 | | 5/1986 | Batina et al. | 128/419 |
| 4,665,896 | | 5/1987 | LaForge et al. | 128/1 |
| 4,679,560 | | 7/1987 | Galbraith | 128/419 |
| 4,741,339 | | 5/1988 | Harrison et al. | 128/419 |
| 4,944,299 | | 7/1990 | Silvian | 128/419 |
| 5,000,178 | | 3/1991 | Griffith | 128/419 |
| 5,214,392 | | 5/1993 | Kobayashi et al. | 330/10 |
| 5,312,439 | | 5/1994 | Loeb | 607/2 |
| 5,324,316 | | 6/1994 | Schulman et al. | 607/61 |
| 5,358,514 | | 10/1994 | Schulman | 607/61 |
| 5,411,537 | | 5/1995 | Munshi et al. | 607/33 |
| 5,527,348 | * | 6/1996 | Winkler et al. | 607/60 |
| 5,621,369 | | 4/1997 | Gardner et al. | 335/302 |
| 5,740,257 | * | 4/1998 | Marcus | 381/71.6 |
| 5,951,459 | | 9/1999 | Blackwell | 600/13 |
| 5,959,522 | * | 9/1999 | Andrews | 336/200 |
| 6,048,601 | | 4/2000 | Yahagi et al. | 428/147 |

OTHER PUBLICATIONS

Altieri et al., "Progress Towards a Totally Impantable Artificial Heart," Cardiovascular Science & Technology: Basic & Applied, 1, Precised Proceedings (1989–90).

Bearnson et al., "Electronics Development for the Utah Electrohydrolic Total Artificial Heart," Sixth Annual IEEE Symposium on Computer–Based Medical Systems, 247–252 (1993).

Callewaert et al., "A Programmable Implantable Stimulator with Percutaneous Optical Control," Ninth Annual Conference of the Engineering in Medical and Biology Society IEEE, 1370–1371 (1987).

Fraim et al., "Performance of a Tuned Ferrite Core Transcutaneous Transformer," *IEEE Transactions on Biomedical Engineering*, BME–18(5):352–59 (1971).

Galbraith et al, "A Wide–Band Efficient Inductive Transdermal Power and Data Link with Coupling Insensitive Gain," *IEEE Transactions on Biomedical Engineering*, BME 34(4):265–275 (1987).

Mitamura et al., "A Transcutaneous Optical Information Transmission System for Implantable Motor–Driven Artificial Hearts," *ASAIO Transactions*, 36(3):M278–280, (1990).

Mitamura et al., "Development of an Implantable Motor –Driven Assist Pump System," *IEEE Transactions and Biomedical Engineering*, 37(2):146–156 (1990).

Mitamura et al., "Development of Motor Driven Assist Pump Systems," IEEE Ninth Conference of the Engineering and Medicine and Biology Society, 184–185, (1987).

Mohammed et al., "A Miniature DC–DC Converter for Energy Producing Implantable Devices," IEEE Ninth Annual Conference of the Engineering in Medicine and Biology Society, 1147–1148, (1987).

Mohammed, "Design of Radio Frequency Powered Coils for Implantable Stimulators," IEEE Ninth Annual Conference of the Engineering in Medicine and Biology Society, 1378–1379, (1987).

Myers, et al., "A Transcutaneous Power Transformer," *Transactions of the American Society for Artificial Internal Organs*, 19:210–14 (1968).

Phillips, "A High Capacity Transcutaneous Transmission System," *ASAIO Journal* 41:m259–m262 (1995).

Product description from Raychem of HeatPath GTQ 1540.

Rintoul et al, "Continuing Development of the Cleveland Clinic–Nimbus Total Artificial Heart," *ASAIO Journal* 39:M168–171 (1993).

Sherman et al., "Transcutaneous Energy Transmission (TET) System for Energy Intensive Prosthetic Devices," *Progress in Artificial Organs* 1985:400–404.

Sutton, "A Miniaturized Device for Electrical Energy Transmission Through Intact Skin—Concepts and Results of Initial Tests," Third Annual Meeting of the International Society for Artificial Organs 5 abstracts (Jul. 1981).

Weiss et al., "A Telemetry System for the Implanted Total Artificial Heart and Ventricular Assist Device," IEEE/Ninth Annual Conference of the Engineering in Medicine and Biology Society 186–187 (1987).

Weiss et al., "Permanent Circulatory Support at the Pennsylvania State University," *IEEE Transaction on Biomedical Engineering* 37(2):138–145 (Feb. 1990).

Yuusuke Abe, et al. "Development of transcutaneous energy transmission system for totally implantable artificial heart," Artificial Heart 2: Proceedings of the $2^{nd}$ International Symposium on Artificial Heart and Assist Device, Edited by Tetsuzo Akutsu, SpringerVerlag Tokyo, Berlin, Heidelberg, New York, London, Paris, 1988.

* cited by examiner

MAGNETIC SHIELD FOR PRIMARY COIL OF TRANSCUTANEOUS ENERGY TRANSFER DEVICE

FIELD OF THE INVENTION

This invention relates to transcutaneous energy transfer (TET) devices and more particularly to an improved primary coil for such device which reduces sensitivity to metal objects in the proximity of the coil and which substantially strengthens the magnetic field output from the coil for a given energy input.

BACKGROUND OF THE INVENTION

Many medical devices are now designed to be implantable, including pacemakers, defibrillators, circulatory assist devices, cardiac replacement devices such as artificial hearts, cochler implants, neuromuscular simulators, biosensors, and the like. Since almost all of the active devices (i.e., those that perform work) and many of the passive devices (i.e., those that do not perform work) require a source of power, inductively coupled transcutaneous energy transfer (TET) and information transmission systems for such devices are coming into increasing use.

These systems consist of an external primary coil and an implanted secondary coil, separated by an intervening layer of tissue. This design generally results in a loosely-coupled transformer with no magnetic shielding. Therefore, transformer parameters, such as mutual and self-inductance values, and the effective series resistance of each coil, can be altered by the presence of conductive objects, for example a metal plate, in the vicinity of the coil. Such parameter changes can result in undesired, and in some cases potentially catastrophic, variations in power delivered to the implanted device. Further, an unshielded primary coil generates a magnetic field which is directed in substantially equal parts toward the secondary coil, where it performs useful work, and way from the secondary coil where the magnetic field energy is substantially wasted. If a higher percentage of the magnetic field from the primary coil could be directed to the implanted secondary coil, the energy required to drive the TET device could be reduced. This could result in the device being driveable from a lower energy, and thus a smaller, lighter and less expensive source, or less drainage on an existing source, facilitating longer battery life between replacement or recharging.

A need therefore exists for an improved primary coil construction for a TET device which both reduces sensitivity of the device to conducting objects in the vicinity of the coils and which increases the percentage of magnetic field generated by the primary coil which reaches the secondary coil, thereby significantly enhancing the energy transfer efficiency of the TET device.

SUMMARY OF THE INTENTION

In accordance with the above, this invention provides a transcutaneous energy transfer device having an external primary coil to which energy to be transferred is applied and an implanted secondary coil inductively coupled to the primary coil and connected to apply energy to a subcutaneous utilization device, the invention being characterized by the inclusion of a magnetic shield covering the primary winding. The shape of the shield is generally substantially the same as that of the primary coil, but the size of the shield should be greater than that of the primary coil. More paiticularly, to fully reflect magnetic field toward the secondary coil, the shield should overlap the primary coil on all sides by at least the thickness (t) of the shield. Where the primary coil has a generally circular shape with a diameter d, the shield has a generally circular shape with a diameter D, where D>d and preferably $D \geq d+2t$. The thickness of the shield for a circular shield is preferably much greater than $D/\mu$ where $\mu$ is the magnetic permeability relative to free space of the shield material, or more generally, $t >> X/\mu$, where X is a major dimension of the shield.

The shield normally has a plurality of ventilation perforations formed therein which perforations are preferably formed parallel to the magnetic field direction so that the path taken through the material of the shield is as short as possible. For embodiments where the primary coil is circular, the perforations are a plurality of radial slots, which slots are slightly wedge-shaped for an illustrative embodiment. To assure adequate ventilation, the perforations should make up between approximately 25% and 75% of the shield area. Since the perforations reduce $\mu$ of the shield material, for the shield thickness to continue to satisfy $t >> X/\mu$, t needs to increase proportionally (i.e., if the shield is 50% perforated, shield thickness $t_p = 2t$). Perforation size should also be small compared the smallest coil in the TET device.

The shield should also be flexible so as to be able to conform to the contours of a patient's body. To achieve this flexibility, for one embodiment of the invention the shield is formed of a low loss magnetic material in a flexible polymer matrix, the shield being formed of a ferrite powder in a silicon rubber for an illustrative embodiment. For another embodiment, the shield is formed of a plurality of segments of a very high permeability material connected by a porous, flexible material. To the extent there are spacings between adjacent segments in a direction substantially perpendicular to the primary coil magnetic field in order to enhance flexibility, such spacings are much smaller than spacings in a direction parallel to the magnetic field.

The shield is also dimensioned and formed of a material which reflects most of the magnetic field directed away from the secondary coil back toward the secondary coil. This significantly enhances the efficiency of energy transfer across the skin boundary by the TET device.

The foregoing and other objects, features and advantages of the invention will be apparent from the following more particular description of preferred embodiments of the invention as illustrated in the accompanying drawings.

IN THE DRAWINGS

DETAILED DESCRIPTION

Figure 1:
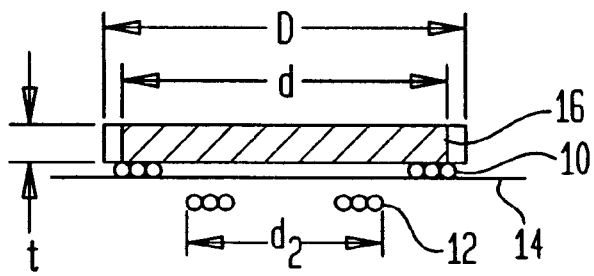
FIG. 1 is a side cutaway view of a TET coil pair with a magnetically shielded primary coil in accordance with the teachings of this invention.

FIG. 1 shows a primary coil 10 having a diameter d and a secondary coil 12 having a diameter $d_2$, where $d_2 < d$, of a TET device for transferring energy through a skin boundary 14. As indicated previously, such a standard TET device has at least two shortcomings. First, the magnetic field of primary coil 10 normally generates substantially equal magnetic fields in directions both toward and away from secondary coil 12. This means that a conductive object in the vicinity of primary coil 10, and in particular a conductive object passing through the magnetic field of this coil, can alter parameters of the coil such as its self-inductance values and effective series resistance, thus resulting in a variation in the energy transferred to secondary coil 12. Since it is desired that this energy transfer be substantially uniform, the potential for spurious variations in energy transfer is at best undesirable, and at worst can have potentially catastrophic consequences for the patient.

A second problem is that energy is required to generate the magnetic field in the direction away from the secondary coil and, since this magnetic field does not contribute to the energy transfer, device efficiency is reduced. Stated another way, the fact that half the magnetic field generated by the primary coil is not being utilized for energy transfer substantially increases the amount of energy which must be applied to the primary coil in order to achieve a desired energy level at the secondary coil.

This invention overcomes both of the problems indicated above by providing a magnetic shield 16 to which the primary windings may be mounted, but which is in any event mounted over primary windings 10. The shape of shield 16 is preferably substantially the same as that of primary coil 10, although this is by no means a limitation on the invention. The size of the shield is also preferably greater than that of the primary winding. Thus, in FIG. 1 it is assumed that both primary winding 10 and shield 16 have a generally circular shape, with the diameter D of the shield shown as being greater than the diameter d of the coil. More specifically, to fully reflect magnetic field toward the secondary coil, shield 16 should overlap primary coil 10 on all sides by at least the thickness (t) of the shield. Thus, for a circular shield, it is preferable that $D \geq d+2t$. For a noncircular coil, having various dimensions $x_i$, the corresponding dimension for the shield would in each instance be $X_i \geq x_i + 2t$.

The thickness (t) of shield 16 should be much greater than $X/\mu_r$ where $\mu_r$ is the magnetic permeability of the magnetic shield material relative to free space and X is a major dimension of the shield. Therefore, for the circular shield of the figures, $t >> D/\mu_r$. For an illustrative embodiment, D=5.5", d=5", t=0.25" and $\mu_r$ is approximately 100. However, the dimensions of the shield will vary significantly with application.

Shield 16 is preferably formed of a low loss magnetic material. This results in the magnetic field emanating from primary coil 10 in the direction of shield 16 being substantially reflected with minimum absorption by the shield, back toward secondary coil 12. With $D \geq d+2t$, substantially all of the magnetic field from the primary coil can be either directed or reflected to the secondary coil, substantially increasing the transfer efficiency of the TET device, this efficiency theoretically being substantially doubled.

While in FIG. 1 the skin surface 14 is shown as being substantially flat, as a practical matter, the skin surface in most applications of this invention will be curved in various ways, requiring that shield 16 be flexible so as to be able to conform to the contours of the skin surface in the transfer area. The material for shield 16 is therefore preferably a low loss magnetic material in a flexible polymer matrix. For one illustrative embodiment of the invention, ferrite powder (Steward MnZn loading powder #73300) is embedded in a silicone rubber in a ratio by weight of 9 parts silicone to 12 parts ferrite powder. Since the polymer in which the magnetic material is embedded significantly reduces the magnetic permeability of the material (the reduction being by a factor of 10 for the illustrative composition), it is desirable to get as much ferrite powder incorporated as possible while retaining the required flexibility of the shield.

Figure 2:
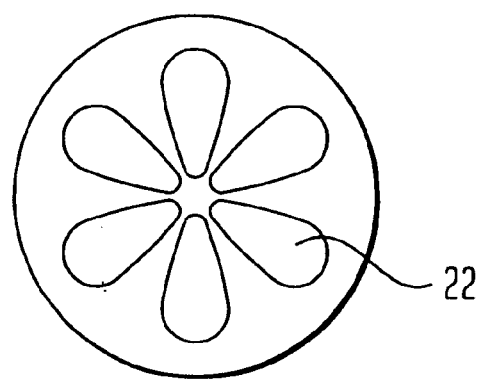
FIG. 2 is a top view of a shield shown in FIG. 1 for one embodiment of the invention.
Figure 3:
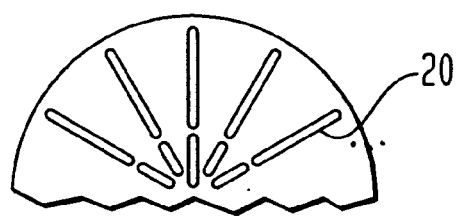
FIGS. 3 and 4 are partial top views of the shield shown in FIG. 1 for two alternative embodiments of the invention.
Figure 4:
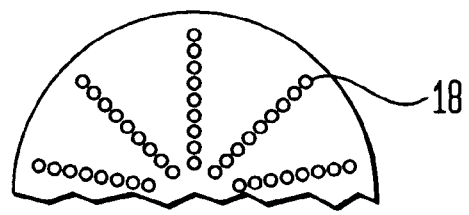

Since the TET device may remain in place for a substantial period of time, it is important that the skin of the patient under shield 16 be able to "breathe", or in other words that air be allowed access to this skin, in order to prevent skin degeneration. It is therefore important that perforation holes be provided in shield 16. Since any openings in the shield may permit potential magnetic field leakage above the shield, the perforations are preferably parallel to the magnetic field in order to minimize magnetic flux paths through the shield material, thus enhancing reflection and minimizing leakage. For the embodiments of FIGS. 2–4, with a circular shield, this means that the perforations should be radial as shown. With other primary coil shapes, the perforation pattern might be different. The smaller and thinner the perforations, the less potential there is for magnetic field leakage, so that the arrangement shown in FIG. 4, with a radially arranged series of small holes 18 is preferable from a shielding standpoint. However, the arrangement of FIG. 4 would not normally provide sufficient ventilation for long-term usage, and an arrangement such as that shown in FIG. 3, with radial slots 20 which are still relatively thin so as to prevent any significant magnetic field leakage, while still providing reasonable ventilation, is therefore generally preferable. More specifically, it has been found that, in order to achieve adequate ventilation, the perforations should make up between 25% and 75% of the area of the shield, with perforations comprising approximately 50% of the area of the shield being generally preferred for long-term usage. This may require a configuration such as that shown in FIG. 2, with generally wedge-shaped slots to increase the perforation area. However, since the existence of the perforations reduces $\mu_r$ for this shield from what it would be without the perforation by an amount which is generally in direct proportion to the percentage of the perforations, and since, as indicated earlier, it is desirable that $t>>D/\mu_r$, this means that t must generally be increased to compensate for the existence of the perforations. For example, if the perforations comprise 50% of the shield area, then the shield thickness $t_p$ must be increased such that $t_p=2t$.

A limitation on perforation size is that the perforation size should be small compared to the size of the smallest coil in the TET device. For the device of FIG. 1, this means that perforations size must be much smaller than that of secondary coil 12. For example, if the diameter of the secondary coil is roughly 1.5 inches, the perforation should be less than approximately 0.5 inches in their smallest dimension. While it should be possible by adjusting shield thickness as well as size and shape of the perforations to minimize magnetic field leakage through the shield, and thus to minimize the interference or loss of energy transfer efficiency caused by a conducting object near or in contact with the shield, it is desirable in any event that the perforations not result in a decrease in coupling efficiency of greater than 20% when a conducting object is brought in contact with the shield.

Figure 5:
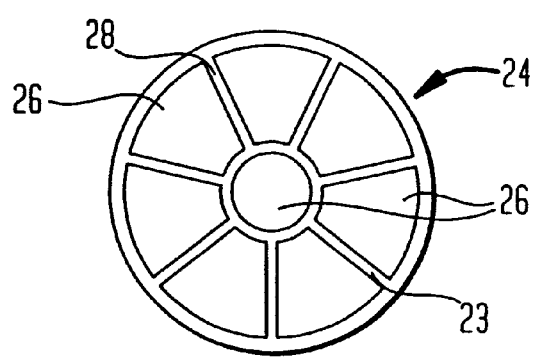
FIG. 5 is a top view of still another embodiment of the invention.

FIG. 5 illustrates a shield 24 which differs from the shields 16 previously discussed in that, instead of being formed of a piece of flexible material having perforations or openings 18–22 formed therein, the shield is formed of segments 26 of a very high permeability but inflexible material, such as a hard ferrite, which segments are connected to each other with a breathable and porous mesh 28 of a polymer or other flexible material. Since the effective $\mu_r$ of the segments 26 is much higher than that of the material used in the flexible shield 16, the shield may be made substantially thinner than for the prior embodiments while still satisfying the requirement that $t>>D/\mu_r$. Thus, a thickness in the order of 1/8 inch or less for shield 24 might be possible, making the shield much more comfortable for the wearer. Further, the high $\mu_r$ segments 26 permit a larger percentage of the area of the shield to be covered by mesh 28 while still achieving desired shielding, enhancing breathability and protecting against skin degeneration. As for the embodiments of FIGS. 1–4, segments 26 may take up 25–75% of the shield area, but would typically take up 50% or less of such area. The radial spacings between segments would, as previously indicated, have a smallest dimension less than the diameter of the secondary coil, and might, for example be 0.5 inches for a roughly 1.5 inch secondary coil. However, the circular spacing, which is required to obtain flexibility in all dimensions for the shield, which spacing is perpendicular to the magnetic field of coil 10, should be much thinner, and for the dimensions above would typically be approximately 0.1 inches. For many applications, the embodiment shown in FIG. 5 may be the preferred embodiment.

While the invention has been particularly shown and described above with reference to several preferred embodiments and variations thereon, it is to be understood that additional variations could be made in the invention by those skilled in the art while still remaining within the spirit and scope of the invention, and that the invention is intended to include any such variations, being limited only by the scope of the appended claims.

What is claimed is:

1. A transcutaneous energy transfer device comprising:
    an external primary coil to which energy to be transferred is applied;
    an implanted secondary coil configured to be inductively coupled to said primary coil and connected to apply energy to a subcutaneous utilization device; and
    a magnetic shield covering a side of said primary coil opposite said secondary coil, wherein said magnetic shield has a plurality of ventilation perforations formed therein.

2. A device as claimed in claim 1 wherein said shield is larger than said primary coil.

3. A device as claimed in claim 2 wherein said primary coil has a selected shape and size, and wherein said magnetic shield is of substantially the same shape as said primary coil, but of greater size.

4. A device as claimed in claim 3 wherein said primary coil has dimensions $x_i$ in direction i, wherein the shield has a thickness t and wherein the dimensions of the shield in direction i is $X_i \geq x_i + 2t$.

5. A device as claimed in claim 3 wherein said primary coil has a generally circular shape with a diameter d, and wherein said shield has a generally circular shape with a diameter D, where D>d.

6. A device as claimed in claim 5 wherein said shield has a thickness t, and wherein $D \geq d+2t$.

7. A device as claimed in claim 5 wherein the shield is formed of a material having a magnetic permeability relative to free space ($\mu_r$) and has a thickness (t), where $t>>D/\mu_r$.

8. A device as claimed in claim 1 wherein the shield is formed of a material having a magnetic permeability relative to free space ($\mu_r$), has a major dimension X, and has a thickness (t) where $t>>X/\mu_r$.

9. A device as claimed in claim 1 wherein said perforations are formed parallel to the magnetic field direction.

10. A device as claimed in claim 9 wherein said primary coil is substantially circular, and wherein said perforations are a plurality of radial slots.

11. A device as claimed in claim 1 wherein said perforations cover approximately 25% to 75% of the area of the shield.

12. A device as claimed in claim 11 wherein said perforations cover approximately 50% of the area of the shield.

13. A device as claimed in claim 11 wherein all dimensions for the perforations are less than the dimensions of the smallest coil in the device.

14. A device as claimed in claim 1 wherein said primary coil has a generally circular shape with a diameter d, and wherein said shield has a generally circular shape with a diameter D, a thickness (t) and is formed of a material having a magnetic permeability relative to free space ($\mu_r$), wherein the perforations result in a reduction $\mu_r$ for the shield which is roughly proportional to the percentage of perforation area, and wherein the shield thickness is increased so as to maintain the relationship $t>>D/\mu_r$.

15. A device as claimed in claim 1 wherein said shield is flexible so as to be able to conform to the contours of a patient's body.

16. A device as claimed in claim 15 wherein said shield is formed of a low loss magnetic material in a flexible polymer matrix.

17. A device as claimed in claim 16 wherein said shield is formed of a ferrite powder in a silicone rubber.

18. A device as claimed in claim 15 wherein said shield is formed of a plurality of segments of a very high permeability material connected by a porous, flexible material.

19. A device as claimed in claim 18 wherein spacings between adjacent segments in a direction substantially parallel to the magnetic field direction of the primary coil is less than the dimensions of the smallest coil in the device, and spacing between adjacent segments in a direction substantially perpendicular to the magnetic field direction is much less than the spacing in said parallel direction.

20. A device as claimed in claim 18 wherein said segments cover approximately 25% to 75% of said shield area.

21. A device as claimed in claim 1 wherein said primary coil generates a magnetic field which is directed both toward and away from said secondary coil and wherein said shield is dimensioned and is formed of a material which reflects most of the magnetic field directed thereto toward said secondary coil.

22. A transcutaneous energy transfer device comprising:
    an external primary coil to which energy to be transferred is applied;
    an implanted secondary coil configured to be inductively coupled to said primary coil and connected to apply energy to a subcutaneous utilization device; and
    a magnetic shield adjacent a side of said primary winding opposite said secondary coil,
        wherein said shield is flexible so as to be able to conform to the contours of a patient's body.

23. A device as claimed in claim 22 wherein said shield is formed of a low loss magnetic material in a flexible polymer matrix.

24. A device as claimed in claim 23 wherein said shield is formed of a ferrite powder in a silicone rubber.

25. A device as claimed in claim 22 wherein said shield is formed of a plurality of segments of a very high permeability material connected by a porous, flexible material.

26. A device as claimed in claim 25 wherein spacings between adjacent segments in a direction substantially parallel to the magnetic field direction of the primary coil is less than the dimensions of the smallest coil in the device, and spacing between adjacent segments in a direction substantially perpendicular to the magnetic field direction is much less than the spacing in said parallel direction.

27. A device as claimed in claim 25 wherein said segments cover approximately 25% to 75% of said shield area.

28. A device as claimed in claim 22 wherein said shield is larger than said primary coil.

29. A device as claimed in claim 28 wherein said primary coil has a selected shape and size, and wherein said shield is of substantially the same shape as said primary coil, but of greater size.

30. A device as claimed in claim 29 wherein said primary coil has a generally circular shape with a diameter d, and wherein said shield has a generally circular shape with a diameter D, where D>d.

31. A device as claimed in claim 30 wherein said shield has a thickness t, and wherein $D \geq d+2t$.

32. A device as claimed in claim 30 wherein the shield is formed of a material having a magnetic permeability relative to free space ($\mu_r$) and has a thickness (t), where $t >> D/\mu_r$.

33. A device as claimed in claim 22 wherein the shield is formed of a material having a magnetic permeability relative to free space ($\mu_r$), has a major dimension X, and has a thickness (t) where $t >> X/\mu_r$.

34. A device as claimed in claim 22 wherein said primary coil generates a magnetic field which is directed both toward and away from said secondary coil and wherein said shield is dimensioned and is formed of a material which reflects most of the magnetic field directed thereto toward said secondary coil.

35. A transcutaneous energy transfer device comprising:
an external primary coil to which energy to be transferred is applied; an implanted secondary coil configured to be inductively coupled to said primary coil and connected to apply energy to a subcutaneous utilization device; and a magnetic shield covering a side of said primary winding opposite said secondary coil,
wherein said shield is a flexible shield formed of a low loss magnetic material in a flexible polymer matrix.

36. A device as claimed in claim 35 wherein said shield is larger than said primary coil.

37. A device as claimed in claim 35 wherein said primary coil has a selected shape and size, and wherein said shield is of substantially the same shape as said primary coil, but of greater size.

38. A device as claimed in claim 37 wherein said primary coil has dimensions $x_i$ in direction i, wherein the shield has a thickness t and wherein the dimensions of the shield in direction i is $X_{i \geq xi}+2t$.

39. A device as claimed in claim 37 wherein said primary coil has a generally circular shape with a diameter d, and wherein said shield has a generally circular shape with a diameter D, where D>d.

40. A device as claimed in claim 35 wherein said shield has a plurality of ventilation perforations formed therein.

41. A device as claimed in claim 40 wherein said perforations are formed parallel to the magnetic field direction.

42. A device as claimed in claim 35 wherein said low loss magnetic material is ferrite powder and said flexible polymer matrix is silicone rubber.

43. A device as claimed in claim 35 wherein said shield is formed of a plurality of segments of a very high permeability material connected by a porous, flexible material.

44. A transcutaneous energy transfer device comprising:
an external primary coil to which energy to be transferred is applied;
an implanted secondary coil configured to be inductively coupled to said primary coil and connected to apply energy to a subcutaneous utilization device; and
a flexible, conforming magnetic shield covering a side of said primary winding opposite said secondary coil, wherein said shield is formed of a plurality of individual segments connected by a porous, flexible material.

45. A device as claimed in claim 44 wherein said plurality of segments comprise segments of a very high permeability material.

46. A device as claimed in claim 44 wherein spacings between adjacent segments in a direction substantially parallel to the magnetic field direction of the primary coil is less than the dimensions of the smallest coil in the device, and spacing between adjacent segments in a direction substantially perpendicular to the magnetic field direction is much less than the spacing in said parallel direction.

47. A device as claimed in claim 44 wherein said shield includes a first side facing said primary coil and a second surface opposite said first side, said first and second sides having a surface area, and wherein said segments cover approximately 25% to 75% of said surface area.

48. A device as claimed in claim 44 wherein said primary coil generates a magnetic field which is directed both toward and away from said secondary coil and wherein said shield is dimensioned and is formed of a material which reflects most of the magnetic field directed thereto toward said secondary coil.

49. A device as claimed in claim 44 wherein said shield is larger than said primary coil.

50. A device as claimed in claim 44 wherein said primary coil has dimensions $x_i$ in direction i, wherein the shield has a thickness t and wherein the dimensions of the shield in direction i is $X_i \geq x_i+2t$.

51. A device as claimed in claim 44 wherein said primary coil has a generally circular shape with a diameter d, and wherein said shield has a generally circular shape with a diameter D, where D>d.

52. A device as claimed in claim 51 wherein said shield has a thickness t, and wherein $D \geq d+2t$.

* * * * *